United States Patent
Addington et al.

(10) Patent No.: US 8,690,790 B2
(45) Date of Patent: *Apr. 8, 2014

(54) TECHNIQUES FOR EVALUATING URINARY STRESS INCONTINENCE

(75) Inventors: W. Robert Addington, Melbourne Beach, FL (US); Stuart Miller, Indialantic, FL (US); Robert E. Stephens, Parkville, MO (US)

(73) Assignee: Pneumoflex Systems, LLC, Melbourne, FL (US)

( * ) Notice: Subject to any disclaimer, the term of this patent is extended or adjusted under 35 U.S.C. 154(b) by 649 days.

This patent is subject to a terminal disclaimer.

(21) Appl. No.: 11/550,125

(22) Filed: Oct. 17, 2006

(65) Prior Publication Data

US 2007/0255090 A1   Nov. 1, 2007

Related U.S. Application Data

(60) Provisional application No. 60/727,740, filed on Oct. 18, 2005, provisional application No. 60/752,351, filed on Dec. 21, 2005.

(51) Int. Cl.
*A61B 5/20* (2006.01)
*A61B 5/03* (2006.01)

(52) U.S. Cl.
USPC .............................................. 600/561

(58) Field of Classification Search
USPC .............................................. 600/561
See application file for complete search history.

(56) References Cited

U.S. PATENT DOCUMENTS

| | | |
|---|---|---|
| 2,918,893 A | 12/1959 | Norton |
| 3,286,713 A | 11/1966 | Kurtz et al. |
| 3,373,735 A | 3/1968 | Gallagher |
| 3,426,758 A | 2/1969 | Harautuneian |
| 3,895,629 A | 7/1975 | Snyder ........................... 128/171 |
| 4,080,970 A | 3/1978 | Miller ........................... 128/350 |
| 4,214,593 A | 7/1980 | Imbruce et al. ............... 128/748 |
| 4,221,215 A | 9/1980 | Mandelbaum ................ 128/155 |

(Continued)

FOREIGN PATENT DOCUMENTS

| | | | |
|---|---|---|---|
| EP | 0 608 593 | 8/1994 | ............... A61B 5/20 |
| EP | 0 694 284 | 1/1996 | ........... A61B 5/0215 |

(Continued)

OTHER PUBLICATIONS

Cormier et al., "*Diagnosis of Female Bladder Outlet Obstruction and Relevance of the Parameter Area Under the Curve of Detrusor Pressure During Voiding: Preliminary Results*," Journal of Urology, May 2002, vol. 167, pp. 2083-2087.

(Continued)

*Primary Examiner* — Rene Towa
*Assistant Examiner* — Emily Lloyd
(74) *Attorney, Agent, or Firm* — Allen, Dyer, Doppelt, Milbrath & Gilchrist, P.A.

(57) ABSTRACT

Techniques for detecting stress urinary incontinence use a pressure sensing catheter the electrical indications of which are applied to a processing unit for detecting pressure levels generated during involuntary coughs. The involuntary coughs are induced preferentially by using a nebulized composition of L-tartrate in a pharmaceutically acceptable carrier. The area under the curve generated from pressure samples is calculated and used in conjunction with the detection of urine leakage to determine the existence of stress urinary incontinence.

4 Claims, 7 Drawing Sheets

(56) References Cited

U.S. PATENT DOCUMENTS

| | | | | |
|---|---|---|---|---|
| 4,613,323 | A | 9/1986 | Norton et al. | 604/43 |
| 4,632,119 | A | 12/1986 | Reichstein | 128/632 |
| 4,790,328 | A | 12/1988 | Young | 600/561 |
| 4,973,314 | A | 11/1990 | Garrett | 604/180 |
| 4,976,261 | A | 12/1990 | Gluck et al. | 128/207.15 |
| 5,146,916 | A | 9/1992 | Catalani | 128/207.14 |
| 5,433,216 | A | 7/1995 | Sugrue et al. | 128/778 |
| 5,462,539 | A | 10/1995 | Herman et al. | 604/385.1 |
| 5,862,804 | A | 1/1999 | Ketchum | 128/885 |
| 5,904,656 | A | 5/1999 | Addington et al. | 600/529 |
| 5,904,666 | A | 5/1999 | Dedecker et al. | 604/65 |
| 5,947,943 | A | 9/1999 | Lee | 604/361 |
| 5,980,507 | A | 11/1999 | Fassuliotis et al. | 604/540 |
| 6,004,268 | A | 12/1999 | Addington et al. | 600/300 |
| 6,056,699 | A | 5/2000 | Sohn et al. | 600/561 |
| 6,267,729 | B1 | 7/2001 | Addington et al. | 604/890.1 |
| 6,284,942 | B1 | 9/2001 | Rabin | 604/361 |
| 6,561,195 | B2 | 5/2003 | Addington et al. | 128/898 |
| 6,568,397 | B1 | 5/2003 | Addington et al. | 128/897 |
| 6,581,605 | B2 | 6/2003 | Addington et al. | 128/897 |
| 6,655,376 | B2 | 12/2003 | Addington et al. | 128/200.24 |
| 6,679,249 | B2 | 1/2004 | Addington et al. | 128/200.14 |
| 6,863,664 | B2 | 3/2005 | Wada et al. | 604/385.17 |
| 7,140,370 | B2 | 11/2006 | Tresnak et al. | 128/207.14 |
| 7,311,696 | B2 | 12/2007 | Christon et al. | 604/385.01 |
| 7,322,359 | B2 | 1/2008 | Kethum | 128/886 |
| 7,332,642 | B2 | 2/2008 | Liu | 604/361 |
| 7,343,915 | B2 | 3/2008 | Addington et al. | 128/203.12 |
| 7,794,425 | B2 | 9/2010 | Gobel | 604/101.05 |
| 2001/0050086 | A1 | 12/2001 | Addington et al. | 128/898 |
| 2002/0049425 | A1* | 4/2002 | Mosel et al. | 604/517 |
| 2002/0112731 | A1 | 8/2002 | Ketchum | 128/866 |
| 2003/0028075 | A1 | 2/2003 | Ulmsten et al. | 600/29 |
| 2003/0078553 | A1 | 4/2003 | Wada et al. | 604/361 |
| 2003/0114809 | A1 | 6/2003 | Gagliardi et al. | 604/361 |
| 2003/0229264 | A1* | 12/2003 | Connors et al. | 600/29 |
| 2004/0015100 | A1 | 1/2004 | Schmidt | 600/561 |
| 2004/0087863 | A1* | 5/2004 | Eide | 600/561 |
| 2004/0116457 | A1* | 6/2004 | Ishihara et al. | 514/290 |
| 2004/0133067 | A1* | 7/2004 | Tracey | 600/29 |
| 2004/0172010 | A1* | 9/2004 | Addington et al. | 604/890.1 |
| 2004/0267336 | A1 | 12/2004 | Morrison et al. | 607/99 |
| 2005/0038328 | A1 | 2/2005 | Stoehrer et al. | 600/301 |
| 2005/0059900 | A1 | 3/2005 | Berger et al. | 600/546 |
| 2005/0065450 | A1 | 3/2005 | Stuebe et al. | 600/547 |
| 2005/0288603 | A1* | 12/2005 | Goping | 600/561 |
| 2007/0123793 | A1 | 5/2007 | Addington et al. | 600/546 |
| 2007/0225576 | A1 | 9/2007 | Brown et al. | 600/301 |
| 2008/0077043 | A1 | 3/2008 | Malbrain et al. | 600/547 |
| 2008/0208151 | A1 | 8/2008 | Zacharias et al. | 604/361 |
| 2008/0255529 | A1 | 10/2008 | Christon et al. | 604/361 |
| 2008/0255530 | A1 | 10/2008 | Christon et al. | 604/361 |
| 2008/0262454 | A1 | 10/2008 | Christon et al. | 604/361 |

FOREIGN PATENT DOCUMENTS

| | | | | |
|---|---|---|---|---|
| WO | 99/53837 | 10/1999 | | A61B 5/08 |
| WO | 03/092495 | 11/2003 | | A61B 5/05 |
| WO | 2004/073516 | 2/2004 | | A61B 5/08 |
| WO | 2004/073516 | 9/2004 | | A61B 5/08 |
| WO | 2007/081626 | 7/2007 | | A61B 5/100 |
| WO | 2008/094771 | 8/2008 | | A61B 10/00 |

OTHER PUBLICATIONS

"Urinary Incontinence in Women" American Family Physician: American Family Physician vol. 62, No. 11 Dec. 1, 2000.

"Exercising Your Pelvic Muscles" American Family Physician: American Family Physician vol. 62, No. 11 Dec. 1, 2000.

Azpiroz et al. "Anorectal Functional Testing: Review of Collective Experience" PMID: 11866256; Am. J. Gastroenterol. Feb. 2002; 97(2)L 2320-240. (Abstract Only).

Bolster et al. "Responses of the Anterolateral Abdominal Muscles During Cough and Expiratory Threshold Loading in the Cat" Journal of Applied Physiology 88: 1207-1214, 2000.

Brown et al. "Prevalence of Urinary Incontinence and Associated Risk Factors in Postmenopausal Women" Obstetrics & Gynecology: 1999: 94: 66-70.

Bump et al. "Cigarette Smoking and Pure Genuine Stress Incontinence of Urine: A Comparison of Risk Factors and Determinants Between Smokers and Nonsmokers" Am. J. Obstet Gynecol. Feb. 1994; 170(2): 579-82. (Abstract Only).

Bump et al. "Valsalva Leak Point Pressures in Women With Genuine Stress Incontinence: Reproducibility, Effect of Catheter Caliber, and Correlations With Other Measures of Urethral Resistance. Continence Program for Women Research Group" Am. J. Obstet. Gynecol. Aug. 1995; 173(2):551-7. (Abstract Only).

Carry et al. "Intra-abdominal Pressure" Ann. Fr. Aneshth. Ranim. 1994; 13(3): 381-99. (Abstract Only).

Chang et al. "Transrectal Sonographic Cystourethrography: Studies in Stress Urinary Incontinence" ScienceDirect-Urology; vol. 36, Issue 6, Dec. 1990, pp. 488-492. (Abstract Only).

Chiara et al. "Expiratory Muscle Strength Training in Persons With Mulitple Sclerosis Having Mild to Moderate Disability: Effect on Maximal Expiatory Pressure, Pulmonary Function, and Maximal Voluntary Cough" Arch Phys Med REhabil. vol. 87, Apr. 2006 pp. 468-473.

Ciofu et al. "Contribution of VLPP (Valsalva Leak Point Pressure) in the Urodynamic Assessment" Gynecol. Obstet. Fertil. Feb. 2004; 32(2): 160-3. (Abstract Only).

Culligan et al. "Urinary Incontinence in Women: Evaluation and Management" American Family Physician, vol. 62 No. 11. Dec. 1, 2000.

Freestone et al."Assessment of the Antitussive Efficacy of Codeine in Cough Associated with Common Cold" PubMed: J. Pharm. Pharmacol. Oct. 1997; 49(10) 1045-1049. (Abstract Only).

Hammond et al. "Assessment of aspiration risk in stroke patients with quantification of voluntary cough" American Academy of Neurology. www.neurology.org 2001;56;502-506.

Hundley et al. "A Multicentered Comparison of Measurements Obtained with Microtip and External Water Pressure Transducers" PubMed: Int. Urogynecol. J. Pelvic Floor Dystfunct. Nov. 12, 2005: 1-7. (Abstract Only).

Kim et al. "The Vesico-Urethral Pressuregram Analysis of Urethral Function Under Stress" ScienceDirect; Journal of Biomechanics, vol. 30. Issue 1, Jan. 1997, pp. 19-25. (Abstract Only).

Kocjancic et al. "Evaluation of Minimally Invasive Analysis System for Cough Leak Point Pressure Measurement" PubMed: J. Uro. Sep. 2004; 172(3): 994-7. (Abstract Only).

Langdon et al. "High Incidence of Respiratory Infections in 'Nil by Mouth' Tube-Fed Acute Ischemic Stroke Patients" Neuroepidemiiology 2009; 32: 107-113.

Lin et al. "comparisons of Urodynamic Characteristics Between Female Patients with Overactive Bladder and Overactive Bladder Plus Stress Urinary Incontinence" ScienceDirect: Urology vol. 64, Issue 5, Nov. 2004, pp. 945-949.

Majoros et al. "Value of Testing the Abdominal Leak Point Pressure in the Differential Diagnosis of Urinary Stress Incontinence" PubMed: Orv. Hetil. Nov. 23, 2003; 144(47): 2321-5. (Abstract Only).

Man et al., "Cough Gastric Pressure and Maximum Expiratory Mouth Pressure in Humans", Am. J. Respir. Crit. Care Med. Sep. 15, 2003;168(6):714-7. Epub Jul. 11, 2003.

Martin, et al. "Systematic review and evaluation of methods of assessing urinary incontinence" Health Technology Assessment, Feb. 2006. vol. 10, No. 6.

Matthys et al. "Objectivation of the Effect of Antitussive Agents Using Tussometry in Patients with Chronic Cough" PubMed: Schweiz Med Wochenschr. Mar. 2, 1985; 115(9): 307-11. (Abstract Only).

McEwan, Jr. et al. "Change in Cough Reflex after Treatment with Enalapril and Ramipril" PubMed: BMJ. Jul. 1, 1989; 299(6690): 13-6. (Abstract Only).

Miklos, Jr. et al. "A Critical Appraisal of the Methods of Measureing Leak-Point Pressures in Women with Stress Incontinence" PubMed: Obstet. Gynecol. Sep. 1995; 86(3): 349-52. (Abstract Only).

Phua, et al. "Patients with Gastro-Oesophageal Reflux Disease and Cough have Impaired Laryngopharyngeal Mechanosensitivity" PubMed: Thorax. Jun. 2005; 60(6): 488-91. (Abstract Only).

(56) References Cited

OTHER PUBLICATIONS

Quek, et al. "*Morbidity and Significant Bacteriuria after Urodynamic Studies*" Annals Academy of Medicine; Singapore 2004; 33:754-7.

Richter, et al. "*Lower Urinary Tract Symptoms, Quality of Life and Pelvic Organ Prolapse: Irritative Bladder an Obstructive Voiding Symptoms in Women Planning to Undergo Abdominal Sacrocolpopexy for Advanced Pelvic Organ Prolapse*" ScienceDirect: Journal of Urology vol. 178, issue 3, Sep. 1997, pp. 965-969.

Shaker, et al. "*Vocal Cord Closure Pressure During Volitional Swallow and other Voluntary Tasks*" PubMed: Dysphagia. 2002 Winter; 17(1)L 13-8. (Abstract Only).

Steffen, et al. "*Measurement of Pressure and Force as a Basis of the Postoperative Evaluation of Abdominal Wall Function*" PubMed: Z. Exp. Chir. Transplant. Kunstliche Organe. 1987; 20(1): 44-9. (Abstract Only).

Swift et al. "*Test-retest Reliability of the Cough Stress Test in the Evaluation of Urinary Incontinence*" Obstetrics and Gynecology; vol. 94, No. 1, Jul. 1999; pp. 99-102.

Van Hengstum, et al. "*Effect of Positive Expiratory Pressure Mask Physiotherapy (PEP) Versus Forced Expiration Technique 9FET/PD) on Regional Lung Clearance in Chronic Bronchitics*" PubMed: Eur. Erspir. J. 1991; 4(6): 651-4. (Abstract Only).

Wall, et al. "*Are Vaginal and Rectal Pressures Equivalent Approximations of One Another for the Purpose of Performing Subtracted Cystometry?*" PubMed: Obstet. Gynecol. Apr. 1995; 85(4):488-93. (Abstract Only).

Bolster et al. "*Neurogenesis of cough, other airway defensive behaviors and breathing: A holarchical system?*" Jan. 16, 2006 www.sciencedirect.com.

DeBacker "*Abdominal compartment syndrome*" http://ccforum.com. Sep. 30, 1999.

Dziewas et al. *Pneumonia in acute stroke patients fed by nasogastric tube* www.jnnp.com Sep. 10, 2003.

Irwin, Richard "*Chronic Cough Due to Gastroesophageal Reflux Disease: ACCP Evidence-Based Clinical Practice Guidelines*" http://chestjournal.chestpubs.org/content/129/1_supll/80S.full.html.

Irwin et al. "*The Cough Reflex and Its Relation to Gastroesophageal Reflux*" Am J Med. 2000;108(4A):73S-78S.

Handa et al. "*Federal Guidelines for the Management of Urinary Incontinence in the United States: Which Patients Should Undergo Urodynamic Testing?*" Int. Urogynecol J (1995) 6:198-203.

Jakus et al. "*Brainstem Areas Involved in the Aspiration Reflex: c-Fos Study in Anesthetized Cats*" Physiol. Res. 53: 703-717, 2004.

Poliacek et al. "*Cough, Expiration and Aspiration Reflexes following Kainic Acid Lesions to the Pontine Respiratory Group in Anesthetized Cats*" Physiol. Res. 53: 155-163, 2004.

Widdicombe et al. "*Supramedullary influences on cough*" Respiratory Physiology Neurobiology 152 (2006) 320-328.

Lavorini et al. "*Fog-induced Cough with Impaired Respiratory Sensation in Congenital Central Hypoventilation Syndrome*" Am J Respir Crit Care med vol. 176. pp. 825-832, 2007.

Lasserson et al., "*Differences in Motor Activation of Voluntary and Reflex Cough in Humans*," Thorax, Aug. 2006; 61(8):699-705. Epub, Apr. 6, 2006.

WD. Man et al., "*Cough Gastric Pressure and Maximum Expiratory Mouth Pressure in Humans*", American Journal of Respiratory and Critical Care Medicine, vol. 168, 2003.

Cadiere et al. "*Antireflux Transoral Incisionless Fundoplication Using EsophyX: 12-Month Results of a Prospective Multicenter Study*" World J Surg (2008) 32:1676-1688.

Marino et al. "*Induction of Lower Esophageal Sphincter (LES) Dysfunction during Use of the Negative Pressure Body Ventilator*" The American Journal of Gastroenterology vol. 83, No. 12, 1988.

"*GERD*" http://www.endogartricsolutions.com/aboutGERD_forsurgeons.htm.

Jones et al. "*Mechanisms of Pelvic Floor Muscle Function and the Effect on the Urethra during a Cough*" www.sciencedirect.com.

Chang et al. "*An objective study of acid reflux and cough in children using an ambulatory pHmetry-cough logger*" http://adc.bmj.com/cgi/reprintform.

Vizel et al. "*Validation of an ambulatory cough detection and counting application using voluntary cough under different conditions*" Http://www.coughjournal.com/content/6/1/3.

Ryan et al. "*Cough reflex sensitivity improves with speech language pathology management of refractory chronic cough*" http://www.coughjournal.com/content/6/1/5.

Canning et al. "*An essential component to brainstem cough gating identified in anesthetized guinea pigs*" The FASEB Journal article fj.09-151068.

F. Lavorini et al., "Fog-Induced Cough with Impaired Respiratory Sensation in Cogenital Central Hypoventilation Syndrome", Am J Respir Crit Care Med., Oct. 15, 2007; 176(8):825-32. Epub Aug. 2007.

Cobb et al., "*Normal Intraabdominal Pressure in Healthy Adults*," Journal of Surgical Research, vol. 129, Feb. 18, 2005, pp. 231-235.

Upadya et al., "*Predictors and Consequences of Pneumonia in Critically Ill Patients With Stroke*,"Journal of Critical Care, vol. 19, No. 1, Mar. 2004, pp. 16-22.

Addington et al. "*Intra-abdominal Pressures during Voluntary and Reflex Cough*" Cough: vol. 4, 2, Apr. 30, 2008; pp. 1-9.

Lasserson et al. "*Differences in Motor Activation of Voluntary and Reflex Cough in Humans*" PubMed: Thorax, Aug. 2006; 61(8): 699-705. (Abstract Only).

\* cited by examiner

| Voluntary Cough |||||||
|---|---|---|---|---|---|---|
| Subject | Test order | AUC | Peak Pressure (cm of water) | Duration (sec.) | No. of Spikes | Leak |
| Subject # 1 | VC $1^{st}$ | 92 | 87 | 3 | 2 | no |
| Subject # 2 | VC $1^{st}$ | 290 | 167 | 6 | 2 | no |
| Subject # 3 | RCT $1^{st}$ | 326 | 100 | 11 | 7 | no |
| Subject # 4 | VC $1^{st}$ | 430 | 165 | 10 | 2 | no |
| Subject # 5 | RCT $1^{st}$ | 612 | 211 | 7 | 5 | yes |
| Subject # 6 | RCT 1st | 518 | 180 | 8 | 5 | yes |

FIGURE 7A

| Involuntary Cough (Reflex Cough Test) |||||||
|---|---|---|---|---|---|---|
| Subject | Test order | AUC | Peak Pressure (cm of water) | Duration (sec.) | No. of Spikes | Leak |
| Subject # 1 | VC $1^{st}$ | 125 | 100 | 3 | 2 | yes |
| Subject # 2 | VC $1^{st}$ | 963 | 175 | 23 | 10 | no |
| Subject # 3 | RCT $1^{st}$ | 1276 | 170 | 27 | 11 | no |
| Subject # 4 | VC $1^{st}$ | 1575 | 139 | 41 | 9 | no |
| Subject # 5 | RCT $1^{st}$ | 1428 | 174 | 26 | 16 | yes |
| Subject # 6 | RCT 1st | 1148 | 194 | 16 | 14 | yes |

FIGURE 7B

TECHNIQUES FOR EVALUATING URINARY STRESS INCONTINENCE

CROSS REFERENCE TO RELATED APPLICATIONS

This application incorporates by reference in its entirety and claims priority to U.S. Provisional Application Ser. No. 60/727,740, filed Oct. 18, 2005, entitled Method of Diagnosing Stress Incontinence by Involuntary Cough by inventor W. Robert Addington, Stuart Miller and Robert Stephens, and claims priority to and incorporates by reference U.S. Provisional Application Ser. No. 60/52,351, filed Dec. 21, 2005, entitled Foley Catheter Having Pressure Transducer by W. Robert Addington and Mary Briganti. This application is related to U.S. patent application Ser. No. 10/783,442, filed Feb. 20, 2004, entitled Apparatus For Evaluating A Patient's Laryngeal Cough Reflex And Associated Methods by W. Robert Addington, Stuart Miller and Robert Stephens, which is incorporated herein by reference in its entirety.

BACKGROUND OF THE INVENTION

1. Field of the Invention

This invention is directed to the field of medical devices and testing and, more particularly, to apparatus and techniques for evaluating urinary stress incontinence.

2. Description of the Prior Art

According to the American Academy of Family Physicians, urinary incontinence (UI) affects approximately twelve million persons in the United States alone. Although urinary incontinence can occur in both men and women, it is most common in women over the age of 50. There are many causes of UI, including age related atrophic changes in the genitourinary anatomy in women after menopause, enlargement of the prostate in men as well as generalized weakening of the pelvic floor muscles, medication side effects, immobility, infection of the urinary tract and various underlying medical co-morbidities including diabetes and hypercalcemia.

There are four basic types of urinary incontinence; functional, overflow, urge and stress. Stress incontinence occurs when there is a sudden pressure on the lower abdominal musculature, such as with a cough, sneeze, laugh or lifting. Stress incontinence is often secondary in part to weakening of the pelvic floor musculature, and is common after childbirth or abdominal surgery. It has been estimated that stress urinary incontinence occurs at least weekly in one third of adult women. (1) Additional reports indicate that more than 65% of female incontinence patients in the United States or 8.3 million women experience stress urinary incontinence. Of these women, approximately 85% or 7 million have incontinence primarily due to hypermobility of the bladder outlet, and approximately 15% or 1.3 million have incontinence primarily due to an intrinsic sphincter deficiency. Regardless of the etiology of UI, for the affected person it maybe a source of significant embarrassment and social isolation. As a result of this social stigma, many patients are reluctant to address this issue with their physician. Most primary care physicians "screen" for urinary incontinence by verbal or written questioning of the patient only. Additional basic evaluation may include a voluntary cough stress test, voiding diary, post void residual urinary volume, and urinalysis. (2)

A patient experiencing urinary incontinence must be properly diagnosed to identify the specific type of incontinence from which the patient suffers. The treatments may be different, depending on the type of incontinence. Therefore, proper diagnosis becomes important at least for that reason.

Stress incontinence may result primarily in older women due to loss of extrinsic support for the pelvic organs and for the neck of the bladder. The tissues of the pelvis and of the distal urethra contain estrogen and progesterone receptors. Following menopause—and decrease of the hormones, the tissues of the urethra may lose resiliency and become somewhat flaccid. Under those conditions, any increase in intra-abdominal pressure causes urine in the bladder to be pushed outwardly as resistance in the urethra is overcome, resulting in leakage of urine. This condition is known as stress incontinence and occurs in the absence of contractions by the detrusor muscle of the bladder. Stress incontinence may be responsive to treatment with exogenous estrogens, although this is not an effective treatment for all patients, particularly depending on age. Alternative treatments may include pelvic muscle exercises, α-adrenergic agents, such as phenylpropanolamine, that act on the a-adrenergic receptors along the urethra and increase urethral tone.

The most common cause of urinary incontinence, however, is detrusor hyperreflexia, or hyperactivity of the detrusor muscle. This type of incontinence is believed to result from lack of inhibition of the detrusor muscle due to a decreased detrusor reflex in the brain stem. Nevertheless, in most affected elderly there appears to be no underlying neurological defect. In this condition, treatment may include antispasmodic agents which tend to relax the wall of the bladder.

A typical test employed to distinguish these two types of urinary incontinence is one which increases intra-abdominal pressure so as to, in turn, put pressure on the bladder. The Valsalva maneuver is one such test. In this technique, the patient generates a muscular contraction of the chest, abdomen and diaphragm in a forced expiration against a closed glottis. This increases pressure within the thoracic cavity and also in the abdominal cavity. The Valsalva maneuver also refers to raising the pressure in the nasopharynx by a forced expiration with the mouth closed and the nostrils pinched, for example, to clear the patency of the Eustachian tubes. Other testing techniques involve having the patient jump up and down to jostle the bladder, or bend down so as to compress the abdomen. Yet another method involves having the patient generate one or more strong voluntary coughs.

It is known, however, that some patients are unable to perform these physical acts. For example, a patient may not be able to jump, or to bend, or to generate a strong voluntary cough. Additionally, there are some patients who will not be correctly diagnosed on the basis of the cough test, perhaps because their coughs are insufficiently strong. Accordingly, there is a need for alternative or supplementary tests that will aid in diagnosing urinary stress incontinence.

A rather complete discussion of methods of evaluating urinary incontinence is found in a February 2006 article by JL Martin et al. entitled "Systematic review and evaluation of methods of assessing urinary incontinence (hereinafter referred to as Systematic review)."

Problems of the Prior Art

One of the problems associated with the prior art techniques is that some patient's are unable or are unwilling to perform the physical acts to the extent needed. For example, a patient may not be able to jump, or to bend, or to generate a strong voluntary cough. For some patient's they maybe able to perform these acts, but be unwilling to do so because an involuntary release of urine maybe embarrassing or contrary to what is considered proper in society.

BRIEF SUMMARY OF THE INVENTION

Various aspects of the invention are directed toward apparatus and techniques for evaluating urinary stress incontinence. Particularly, the invention is directed toward evaluating urinary stress incontinence using a reflexive cough test (RCT), which triggers an involuntary cough on the part of the patient. Such an involuntary cough overcomes some of the problems of prior art techniques and produces a more reliable test for urinary stress incontinence.

BRIEF DESCRIPTION OF THE DRAWINGS

The invention will be described more in detail with reference to the following drawings.

DETAILED DESCRIPTION OF THE INVENTION

Figure 1:
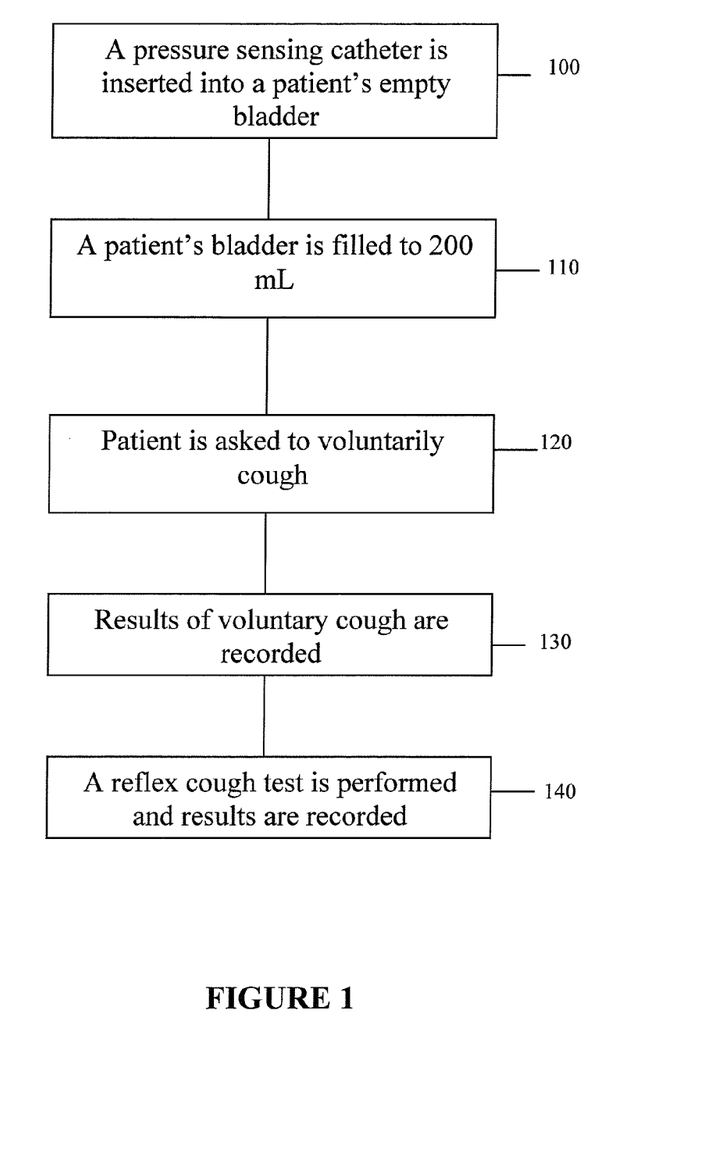
FIG. 1 shows a flow chart of a technique for evaluating a patient for urinary stress incontinence in accordance with one aspect of the invention.

FIG. 1 shows a flow chart of a technique for evaluating a patient for urinary stress incontinence in accordance with one aspect of the invention. As an initial step, pressure sensing catheter is inserted into a patient's empty bladder (100). The patient's bladder is then filled slowly with sterile water until 200 ml have been delivered (110).

The patient is then asked to voluntarily cough (120) and the results of the voluntary cough are recorded (130) by recording the variations in pressure as a function of time and by recording whether or not the cough induced involuntary expulsion of urine. See item 130.

Then, a reflex cough test is performed (140) and the results are recorded in a manner substantially similar to step 130. Details of the reflex cough tests are discussed more in conjunction with FIG. 2.

Figure 2:
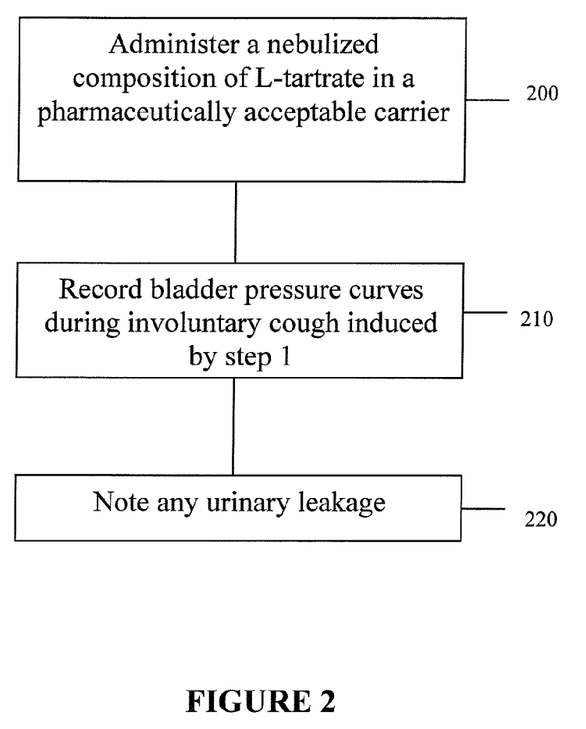
FIG. 2 shows a flow chart of a technique for conducting a reflexive cough test (RCT).

FIG. 2 shows a flow chart of a technique for conducting a reflex cough test. With the test arrangement in place as described in conjunction with items 100 and 110 of FIG. 1, instead of asking a patient to voluntarily cough, the patient is administered a nebulized composition of L-tartrate in a pharmaceutically acceptable carrier (200). The variations in bladder pressure that occur during the involuntary coughs induced by step 200 are then recorded and plotted for display (210). The patient is checked for any urinary leakage that occurs during the involuntary coughs (220).

Figure 3:
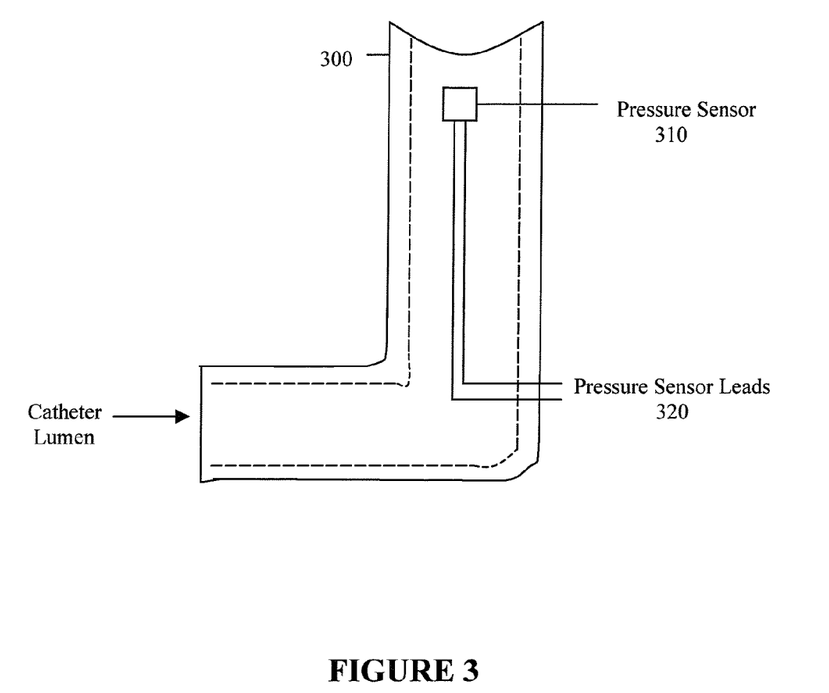
FIG. 3 shows a catheter that can be used for carrying out various aspects of the invention.

FIG. 3 shows a catheter that can be used for carrying out various aspects of the invention. A catheter, 300, includes a pressure sensor 310 and conductive wires or paths which conduct the electrical output of the pressure sensor 310 to external circuitry. The wires or paths are hereinafter called pressure sensor leads 320. The catheter lumen can be utilized to fill or drain the patient's bladder as appropriate. Examples of a catheter usable in accordance with the invention may include a Foley catheter equipped with a pressure sensor.

Figure 4:
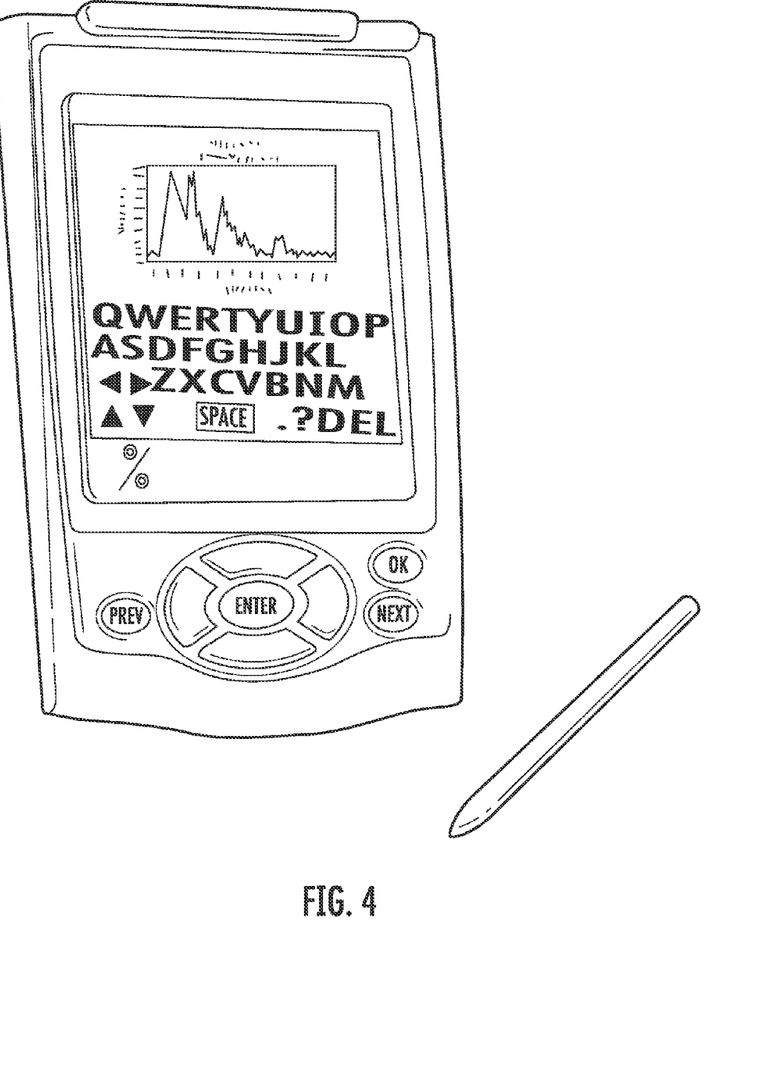
FIG. 4 is an illustration of a hand held processing device that can be used to carry out the invention.

FIG. 4 is an illustration of a hand held processing device that can be used to carry out the invention. As shown on the device display screen, the variation in pressure that occurs as a function of time during a voluntary or involuntary cough is displayed.

Figure 5:
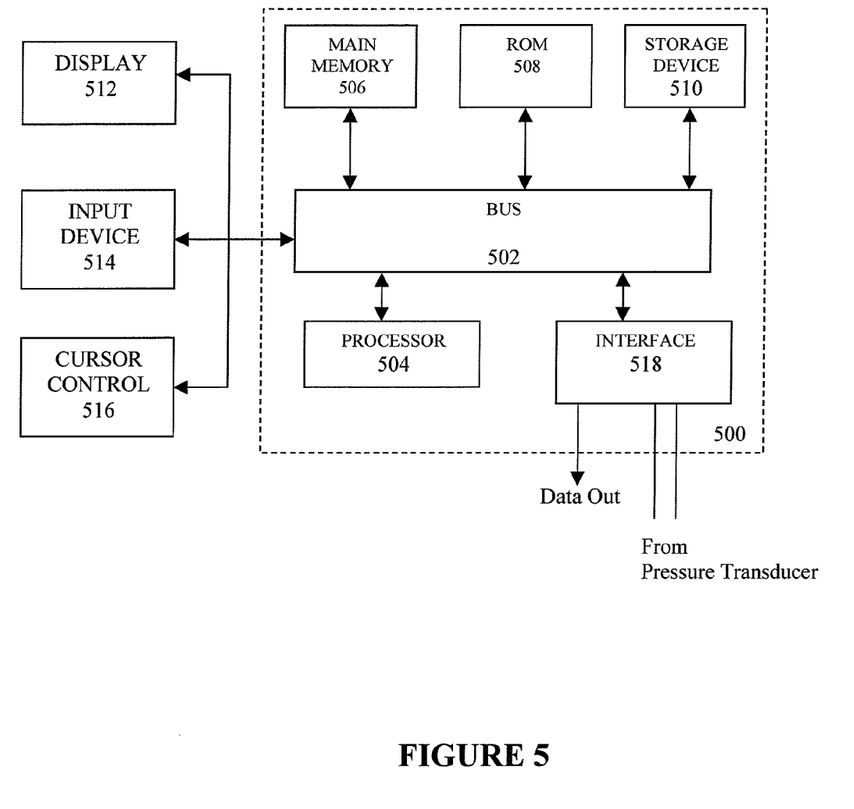
FIG. 5 is a block diagram of an exemplary processing device that can be used to carry out aspects of the invention.

FIG. 5 is a block diagram of an exemplary processing device that can be utilized to carry out aspects of the invention. FIG. 5 is a block diagram that illustrates a computer system 500 upon which an embodiment of the invention may be implemented. Computer system 500 includes a bus 502 or other communication mechanism for communicating information, and a processor 504 coupled with bus 502 for processing information. Computer system 500 also includes a main memory 506, such as a random access memory (RAM) or other dynamic storage device, coupled to bus 502 for storing information and instructions to be executed by processor 504. Main memory 506 also may be used for storing temporary variables or other intermediate information during execution of instructions to be executed by processor 504. Computer system 500 further includes a read only memory (ROM) 508 or other static storage device coupled to bus 502 for storing static information and instructions for processor 504. A storage device 510, such as a magnetic disk or optical disk, is provided and coupled to bus 502 for storing information and instructions.

Computer system 500 may be coupled via bus 502 to a display 512, such as a cathode ray tube (CRT), for displaying information to a computer user. An input device 514, including alphanumeric and other keys, is coupled to bus 502 for communicating information and command selections to processor 504. Another type of user input device is cursor control 516, such as a mouse, a trackball, or cursor direction keys for communicating direction information and command selections to processor 104 and for controlling cursor movement on display 512. This input device typically has two degrees of freedom in two axes, a first axis (e.g., x) and a second axis (e.g., y), that allows the device to specify positions in a plane.

Computer system 500 operates in response to processor 504 executing one or more sequences of one or more instructions contained in main memory 506. Such instructions may be read into main memory 506 from another computer-readable medium, such as storage device 510. Execution of the sequences of instructions contained in main memory 506 causes processor 504 to perform the process steps described herein. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 504 for execution. Such a medium may take many forms, including but not limited to, non-volatile media, volatile media, and transmission media. Non-volatile media includes, for example, optical or magnetic disks, such as storage device 510. Volatile media includes dynamic memory, such as main memory 506. Transmission media includes coaxial cables, copper wire and fiber optics, including the wires that comprise bus 502. Transmission media can also take the form of acoustic or light waves, such as those generated during radio-wave and infra-red data communications.

Common forms of computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 504 for execution. For example, the instructions may initially be carried on a magnetic disk of a remote computer. The remote computer can load the instructions into its dynamic memory and send the instructions over a telephone line using a modem. A modem local to computer system 500 can receive the data on the telephone line and use an infra-red transmitter to convert the data to an infra-red signal. An infra-red detector can receive the data carried in the infra-red signal and appropriate circuitry can place the data on bus 502. Bus 502 carries the data to main memory 506, from which processor 504 retrieves and executes the instructions. The instructions received by main memory 506 may optionally be stored on storage device 510 either before or after execution by processor 504.

Figure 6:
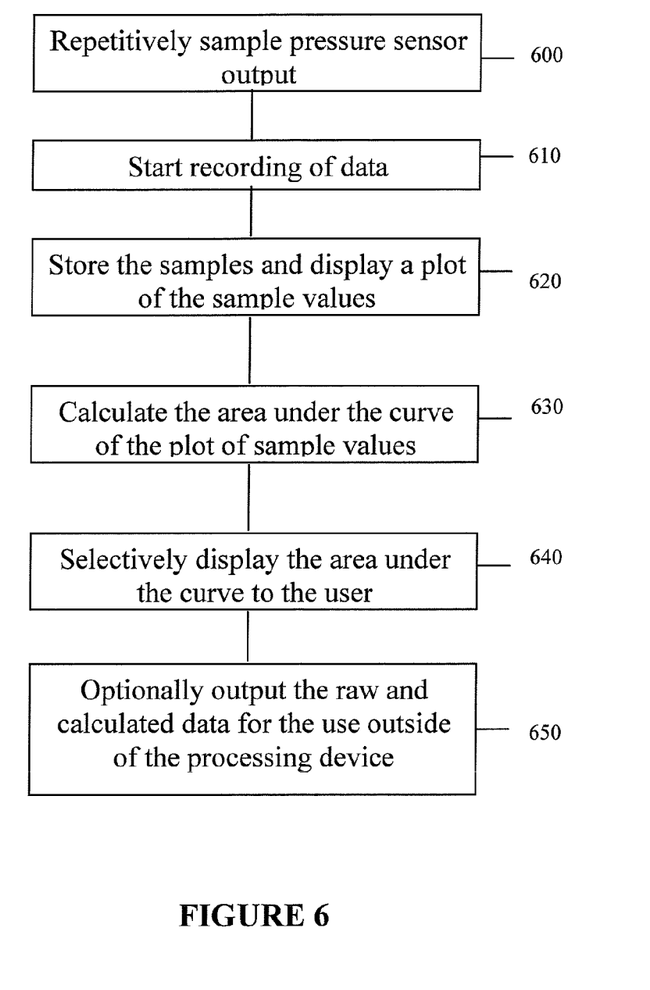
FIG. 6 is a flow chart of software use to program a processing device in accordance with one aspect of the invention.

FIG. 6 is a flow chart of software used to program a processing device in accordance with one aspect of the invention. The processing device is programmed to repetitively sample pressure output from the sensor (600). Upon receipt of an initiation or start signal, the processor can start recording data from the pressure sensor (610). The start signal can be generated by utilizing either a rapid increase in pressure, by detecting a pressure threshold being exceeded, or by receiving a trigger signal initiated by a user. Such a signal was discussed in conjunction with U.S. patent application Ser. No. 10/783,442, filed Feb. 20, 2004, entitled Apparatus For Evaluating A Patient's Laryngeal Cough Reflex And Associated Methods, by W. Robert Addington, Stuart Miller and Robert Stephens, referred to above.

After receipt of the starts signal, the processing unit stores the samples and displays the plot of the pressure sample values (620).

Upon completion of the cough sequence, software is programmed to calculate the area under the curve of a plot of the sample values (630). The areas under the curve (AUC) values are calculated by the numerical integration of intravesical pressure over time with either Simpson's ⅜-rule or Bode (or Boole's) rule. Both Simpson's ⅜-rule and Bode (or Boole's) rule are methods of numerical integration that yield more accurate results for AUC than the trapezoidal method.

Simpson's ⅜ rule $$\int_\alpha^\beta f(x)dx \approx \frac{3h}{8}(f_0 + f_n + 3(f_1 + f_4 + \ldots + f_{n-2}) + 3(f_2 + f_5 + \ldots + f_{n-1}) + 2(f_3 + f_6 + \ldots + f_{n-3}))$$

$$= \frac{3h}{8}\left\{f(\alpha) + f(\beta) + 3\sum_{i=1,4,7,\ldots}^{n-2} f(\alpha + ih) + 3\sum_{i=2,5,8,\ldots}^{n-1} f(\alpha + ih) + 2\sum_{i=3,6,9,\ldots}^{n-3} f(\alpha + ih)\right\}$$

Bode's (Boole's) rule $$\int_{x_1}^{x_5} f(x)dx = \frac{2}{45}h(7f_1 + 32f_2 + 12f_3 + 32f_4 + 7f_5) - \frac{8}{945}h^7 f^{(6)}(\xi).$$

All AUC values were calculated using Bode's (Boole's) rule, except for that of Patient #1, which was calculated with Simpson's ⅜-rule. Bode's (Boole's) method was not very adept at handling as few data points (3).

The process may selectively display the calculated area under the curve to the user either with or separately from display of the plot of the sample values (640).

Optionally, one may output the raw and calculated data for use outside of the processing device (650). This can be done utilizing interface 518.

Figure 7A:
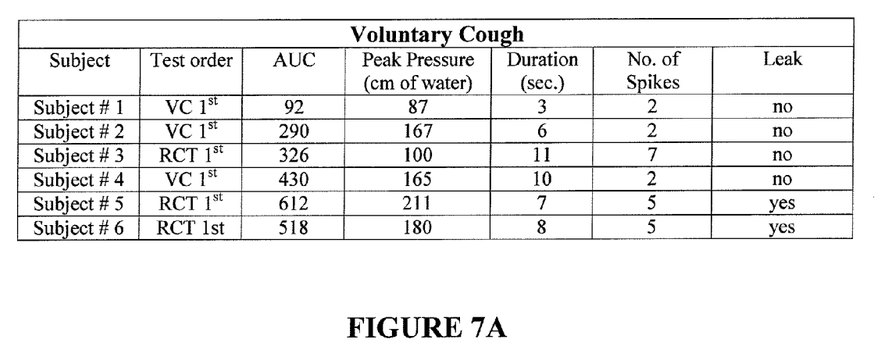
FIG. 7A and 7B illustrate test results comparing voluntary cough and involuntary cough techniques for assessing stress urinary incontinence.
Figure 7B:
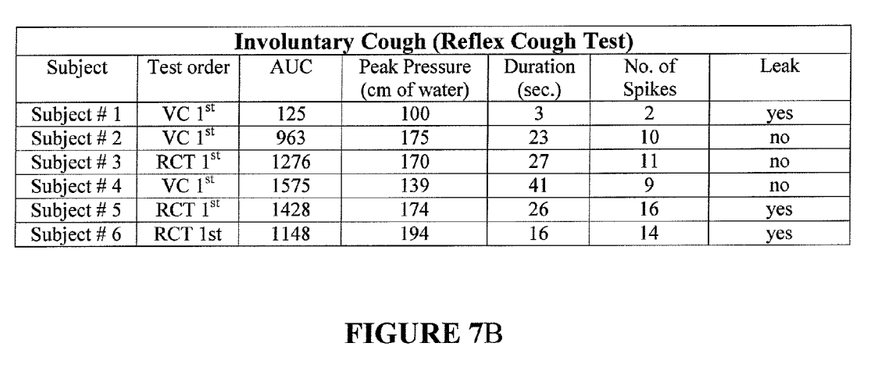

FIG. 7A and 7B illustrate test results comparing voluntary cough and involuntary cough techniques for assessing stress urinary incontinence.

The testing that produced the results shown in FIG. 7A and 7B are described as follows.

Objective

The objective of this study were to:
1. Evaluate the effectiveness of the reflex cough test (RCT) versus voluntary cough in confirming stress urinary incontinence in female subjects with a history of mild urinary incontinence as determined by the Incontinence Quality of Life Instrument (I-QOL); and
2. Correlate, if indicated, intravesicular pressure measurements with urinary leakage after RCT.

Materials and Methods

Voluntary and involuntary (RCT) cough provocation maneuvers were performed during urodynamic testing in 6 women. Four women had a history of mild stress urinary incontinence and two were normal controls. The order of the cough provocation procedures was randomized.

Prior to urodynamic assessment, subjects were instructed to empty the bladder (confirmed via ultrasound). Using sterile technique, calibrated bladder and rectal catheters were placed and continuous dual-channel pressure recording was performed and the subject's bladder was filled slowly with sterile water until 200 mL had been delivered.

Cough Leak Point Pressure (CLPP) was assessed with a bladder volume of 200 mL. Leakage was determined by visual inspection of the perineum by the Investigator during the coughs, and electronically marked on the print-out. If the subject did not leak with either cough maneuver in the semi-recumbent position, the standing position was used. Urodynamic testing was completed with filling to capacity to observe for detrusor instability.

After instruction, subjects performed a maximal forceful voluntary cough (VC) and an involuntary cough. The involuntary cough was elicited by stimulating the laryngeal cough reflex by performing the RCT with the patient's nose held closed. The RCT involves inhaling a concentration of 20% L-(+)-tartaric acid dissolved in normal, sterile saline (Nephron Pharmaceuticals, Orlando, Fla.) delivered via jet nebulizer.

An independent reviewer used the continuous pressure recording of each subject to determine peak pressures, measure duration of the cough events, count the number of pressure spikes, and derive area under the curve (AUC) numbers.

Results

Peak pressures were similar when comparing voluntary cough with the RCT (FIGS. 7A and 7B). Duration of cough events, AUC, and number of spikes were all increased with RCT relative to voluntary cough. Neither of the 2 normal subjects leaked with either cough maneuver. Of the 4 subjects with mild stress urinary incontinence (diagnosed by I-QOL), 3 leaked with RCT and 2 leaked with VC. A possible carry-over effect was identified when assessing subjects that were randomized to undergo RCT testing prior to VC. There appear to be a relative increase in AUC, peak pressure, duration, and in the number of spikes with VC testing when voluntary cough testing was performed after, rather then prior art to, the RCT (FIGS. 7A and 7B). It is notable that both subjects that leaked with voluntary cough were randomized to have the RCT performed first.

Conclusion

RCT provides considerable "stress" in subjects with stress urinary incontinence and appears to be a useful involuntary maneuver in eliciting leakage in subjects with this condition. No other involuntary maneuver has been studied in evaluating this condition. The data suggests that RCT may be more efficient in provoking leakage in subjects with stress urinary incontinence than voluntary cough.

The present invention has been described above, in which description preferred embodiments of the invention are discussed. Unless otherwise defined, technical and scientific terms used herein have the same meaning as commonly understood by one of ordinary skill in the art to which this invention pertains. Although methods and materials similar or equivalent to those described herein can be used in the practice or testing of the present invention, suitable methods and materials are described above. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided solely for exemplary purposes so that this disclosure will be thorough and complete, and will fully convey the scope of the invention to those skilled in the art. Other features and advantages of the invention will be apparent from the above detailed description, and from the claims.

What is claimed is:

1. A method for evaluating for stress urinary incontinence, comprising:
    inserting a pressure sensing catheter within a patient's bladder, the pressure sensing catheter having a pressure sensor on the surface of the catheter and positioned within the patient's bladder for measuring bladder pressure;
    filling the patient's bladder to a predetermined level;
    having the patient voluntarily cough to produce a voluntary cough event;
    sampling pressure output values from the pressure sensing catheter for the duration of the voluntary cough event corresponding to the intravesical pressure;
    calculating the area under the curve (AUC) by integrating the sampled values of intravesical pressure over time;
    determining a peak intravesical pressure value for the duration of the voluntary cough event;
    determining if there has been an involuntary expulsion of urine during the voluntary cough event;
    supplying to the throat of the patient an aerosol containing a chemoirritant agent effective for inducing an involuntary cough event;

sampling pressure output values from the pressure sensing catheter for the duration of the involuntary cough event corresponding to the sampled intravesical pressure;

calculating the area under the curve (AUC) by integrating the intravesical pressure samples over time;

determining a peak intravesical pressure value for the duration of the involuntary cough event; and determining if there has been an involuntary expulsion of urine during the involuntary cough event;

processing values for the AUC of the voluntary and involuntary cough events, the peak intravesical pressure values for the voluntary and involuntary cough events and correlating to whether there was any involuntary expulsion of urine during the voluntary and involuntary cough events to evaluate the patient for stress urinary incontinence.

2. The method according to claim 1, and further comprising plotting the measured variations in bladder pressure on a graph and calculating an area under the curve for the graph.

3. The method according to claim 1, and further comprising inducing the involuntary cough event by administering to the patient a nebulized composition of L-tartrate in a pharmaceutically acceptable carrier.

4. The method according to claim 1, and further comprising processing within a hand held unit.

* * * * *